United States Patent [19]

Wilkerson

[11] Patent Number: 5,445,603
[45] Date of Patent: Aug. 29, 1995

[54] THERAPEUTIC ANKLE ORTHOSIS

[76] Inventor: Gary B. Wilkerson, 1104 Bacon Blvd., Madisonville, Ky. 42431

[21] Appl. No.: 169,149
[22] Filed: Dec. 17, 1993
[51] Int. Cl.⁶ .............................................. A61F 5/00
[52] U.S. Cl. ........................................ 602/27; 602/23
[58] Field of Search .................... 602/5, 16, 23, 27–29; 128/882

[56] References Cited

U.S. PATENT DOCUMENTS

| | | | |
|---|---|---|---|
| 3,779,654 | 12/1973 | Horne | 602/16 X |
| 4,590,932 | 5/1986 | Wilkerson | 602/27 X |
| 4,719,926 | 1/1988 | Nelson | 602/27 |
| 4,865,023 | 9/1989 | Craythorne et al. | 602/27 |
| 5,031,607 | 7/1991 | Peters | 602/27 |
| 5,044,360 | 9/1991 | Janke | 602/27 X |
| 5,069,202 | 12/1991 | Prock | 602/27 |
| 5,242,379 | 9/1993 | Harris et al. | 602/27 |

Primary Examiner—Linda C. M. Dvorak
Attorney, Agent, or Firm—Charles J. Brown

[57] ABSTRACT

A therapeutic ankle orthosis including overlapping lateral and foot shells pivotally interconnected to permit pivotal foot movement about the talocrual joint with the overlapping portions of the lateral and foot shells secured together to protect against ankle ligament injury from rotation of the foot and leg in opposite directions in the horizontal plane.

29 Claims, 3 Drawing Sheets

THERAPEUTIC ANKLE ORTHOSIS

BACKGROUND OF THE INVENTION

At the outset a distinction is to be made between functional ankle braces and therapeutic ankle orthoses. An ankle brace is designed to limit the range of side-to-side foot motion during stressful functional activities. An ankle orthosis, on the other hand, serves as a functional ankle brace during the transitional period between resolution of acute sprain symptoms and complete restoration of normal ankle function and at the same time therapeutically treats and controls residual sprain symptoms.

An example of an ankle brace of the prior art is that disclosed in U.S. Pat. No. 5,069,202. Its structure includes a foot shell pivoted to a leg shell which comprises lateral and medial uprights connected by an anterior band. Adjustable strap means are included for holding these components in operative position on the leg, ankle and foot. Another form of ankle brace is disclosed in U.S. Pat. No. 5,199,941 which includes medial and lateral shells connected to a foot shell, though without a pivotal joint between them. A therapeutic ankle orthosis is disclosed in U.S. Pat. No. 4,556,054 and includes a foot shell and a leg cuff interconnected by appropriate adjustable straps.

That prior art disclosure perhaps most pertinent to the present invention is German Gebrauschmuster (or Petty Patent) No. 6 88 14 157.8 published on Feb. 9, 1989. It is intended to function therapeutically during recovery from acute sprain symptoms and at the same time to brace the ankle to limit the maximum range of side-to-side foot motion. The therapeutic functions include compression and joint stabilization. This German Petty Patent teaches a foot shell pivotally and slidably connected to the lower end of lateral and medial shells by means of a post in a curved slot, with the components held together by adjustable strap means. The lateral shell includes an aperture for encircling the fibular malleolus and an inner pad for compression. The pad is not of U-shape, though pads of that configuration are known from such prior art patents as my U.S. Pat. No. 4,590,932 to disperse edema upwardly from those regions around the fibular malleolus where excess fluid accumulates.

The most common mechanism causing ankle ligament injury is inversion or turning inward of the sole of the foot. However, there is an associated mechanism which involves rotation of the foot and leg in opposite directions in a horizontal plane, referred to as adduction of the foot or internal foot rotation combined with external leg rotation. Prior art ankle braces emphasize means for restraining inversion of the foot but do little to protect against external rotation of the leg upon a foot that is fixed to the ground.

In the German Petty Patent referred to above the articulation of the foot shell with respect to the lateral shell by means of a curved slot and rivet allows for a combination of rotational and gliding movement between the components. The curvature of the slot does not correspond to the functional axis of the upper ankle joint, namely the talocrual joint. Rotation of the foot and leg in opposite directions in a horizontal plane would result in a spreading apart of the lateral and foot components of the German Petty Patent along the anterior margin of the overlapped areas. Such a design does not provide resistance to rotary ankle motion within the horizontal plane.

SUMMARY OF THE INVENTION

The therapeutic ankle orthosis of the invention includes an extended lateral shell having an aperture for receiving the fibular malleolus and having a lower end portion extending downwardly beneath that aperture. A crescent-shaped medial shell is adapted to fit beneath and upwardly about the tibial malleolus. A foot shell is adapted to underlie the rear foot and extend forwardly, preferably beyond the tarsal joint, and has an upper lateral side portion extending upwardly to overlap the lower end portion of the lateral shell. Pivoting means connect the lower end portion of the lateral shell to the side portion of the foot shell permitting ankle movement of the foot shell relative to the lateral shell about an axis substantially coincident with the functional axis of the talocrual joint. Locking means are included for selectively preventing ankle movement of the foot shell relative to the lateral shell. Securing means are provided for holding together the overlapping end portion of the lateral shell and the side portion of the foot shell forwardly of the pivot means to resist ankle inversion and eversion. Adjustable strap means are included for holding the shells in operative position on the leg and ankle and foot.

The lateral shell may be contoured generally to fit the lower leg and ankle and may include a curved posterior leg brace portion. A U-pad may be secured to the inside of the lateral shell and a crescent pad may be secured to the inside of the medial shell. The lateral shell lower end portion may overlap outside of the foot shell side portion. The pivot means may be a rivet fixed to the foot shell side portion and extending outwardly through a hole in the overlapping lateral shell end portion and having a head holding the overlapping side and end shell portions together.

A curved slot may be formed in either of the overlapping lateral shell end portion or the foot shell side portion. The curve of the slot may be centered about the axis of the pivot means. One end of the slot may be approximately horizontally forward of the pivot means axis and the other end of the slot should be at least about 45° downwardly and forwardly of the pivot means axis when the leg and foot is horizontal and vertical respectively. The slot may be formed in the lateral shell lower end portion and the lower end portion may overlap the outside of the foot shell side portion.

The locking means may comprise removable locking screws extending through the slot at each end thereof into threaded engagement with the overlapping lateral shell end portion and foot shell side portion. When the slot is formed in the lateral shell lower end portion and the lower end portion overlaps the outside of the foot shell side portion, the removable locking screws are in threaded engagement with the foot shell side portion.

The securing means may comprise a post affixed to that overlapping shell portion in which the curved slot is not formed. This post may extend through the slot intermediate the ends thereof when the leg and foot are vertical and horizontal respectively. On the outer end of the post there may be a cap for holding the shell portion in which the slot is formed against the other shell portion. When the slot is formed in the lateral shell lower end portion and the lower end portion overlaps the outside of the foot shell side portion, the post is then affixed to the foot shell side portion.

The strap means may comprise a first strap fixed at one end to a forward portion of the foot shell and threaded through first slots in the medial shell and adjustably secured at the opposite end to buckling means above the overlapping shell portions. A second strap may be provided which is fixed at one end to a rearward portion of the foot shell and threaded through second slots in the medial shell and adjustably securable at its opposite end to the buckling means. A foot strap may be included which is affixed at one end to one side of the foreward portion of the foot shell and threaded through a slot in the opposite side of the foreward position of the foot shell and turned back upon and adjustably secured to itself. There may be a leg strap affixed at one end to the upper portion of the lateral shell and adjustably secured at its opposite end to the upper portion of the lateral shell.

The medial shell may be movable up and down and forward and rearward, with the first and second straps sliding in their respective medial shell first and second slots, to locate the medial shell in a selected position relative to a user's tibial malleolus. The first and second and foot straps may be affixed to the underside of the medial side of the forward portion of the foot shell. The buckling means for the first and second straps may overlie the lateral shell aperture.

The shells are preferably semi-rigid, by which is meant that they are stiff enough so that the foot shell, for example, does not significantly lose its foot-contoured shape under normal maximum adult weight, but flexible enough to be depressed to exert extra localized pressure against the ankle behind a tightly fitted strap.

DESCRIPTION OF PREFERRED EMBODIMENT

Figure 1:
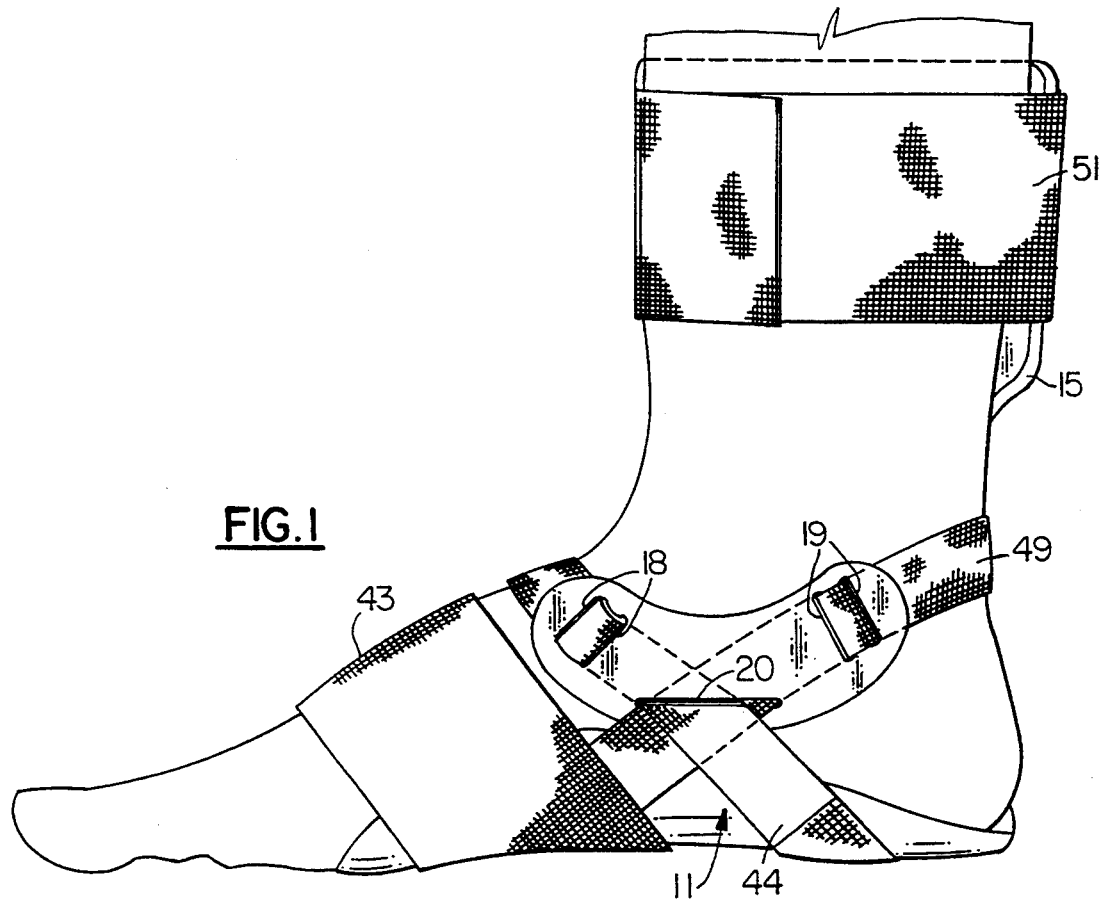
FIG. 1 is an elevation of the therapeutic ankle orthosis of the invention viewed from the medial side and fully assembled on a leg and ankle and foot.

Referring first to FIGS. 1 to 4, the therapeutic ankle orthosis of the invention includes three semi-rigid shells, namely an extended lateral shell 10, a foot shell 11 and a crescent-shaped medial shell 12. Each of the shells is of unitary molded plastic construction, perhaps of varying thickness to vary the degree of semi-rigidity in different portions of each shell. Polypropylene or polyethylene may be a suitable material for the shells. Each is contoured to fit generally against typical leg, ankle and foot anatomy against which it is disposed during use.

The lateral shell 10 fits against and is contoured to the lateral side of the lower leg and ankle and includes an aperture 13 to receive the fibular malleolus. Extending downwardly beneath the aperture 13 is a lower shell end portion 14. A curved posterior leg brace portion 15 is included at the upper end of the lateral shell 10 to fit around the back of the leg. If desired a similar curved anterior leg brace portion could be included to make the lateral shell 10 symmetrical about its vertical longitudinal axis and therefore be reversible to fit on either the left or the right foot and ankle. A first pair of side-by-side slots 16 and a second pair of side-by-side slots 17 are equally spaced on opposite sides of the aperture 13.

Figure 4:
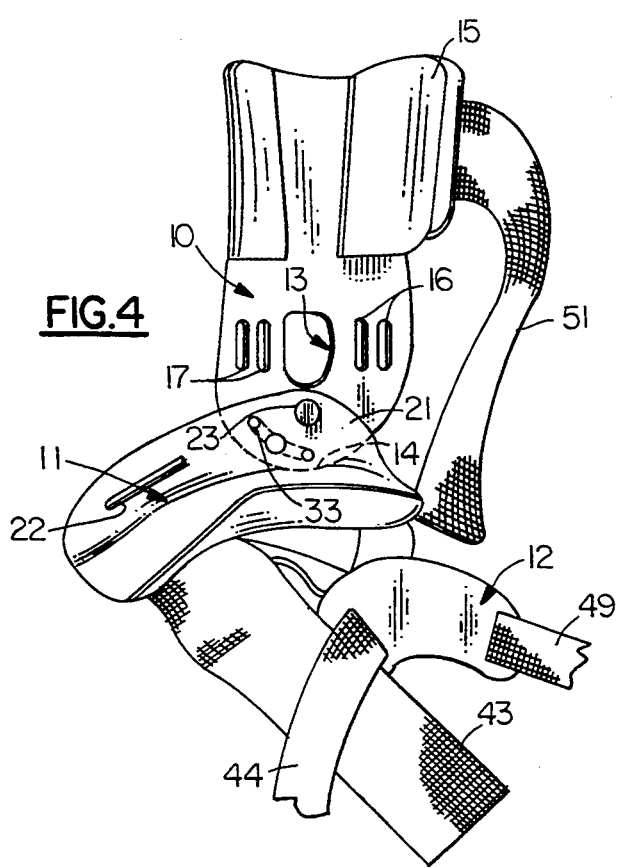
FIG. 4 is a perspective view of certain of the disassembled components of the therapeutic ankle orthosis of the invention.

The crescent-shaped medial shell 12 shown in FIGS. 1 and 4 is adapted to fit beneath and upwardly about the tibial malleolus. It is of symmetrical configuration and can be used on either the left or the right ankle. It includes a first pair of side-by-side slots 18 at one end and a second pair of side-by-side slots 19 at its opposite ends. Between those pairs of slots is a wider central slot 20.

The foot shell 11 is adapted to underlie the rear foot and extend forwardly beyond the tarsal joint. It is in the form of a contoured stirrup which includes an upper lateral side portion 21. A slot 22 is defined in the lateral side portion of the foot shell 11 forwardly of the upper lateral side portion 21.

A rivet 23 provides pivot means connecting the lower end portion 14 of the lateral shell 10 to the upper side portion 21 of the foot shell 11. The rivet 23 is affixed to the foot shell side portion 21 and extends outwardly through a larger hole in the overlapping lateral shell lower end portion 14. A head 25 on the rivet 23 holds the overlapping side and end shell portions 21 and 14 together and at the same time permits angular movement of the foot shell 11 relative to the lateral shell 10 about an axis substantially coincident with the functional axis of the talocrual joint.

Figure 2:
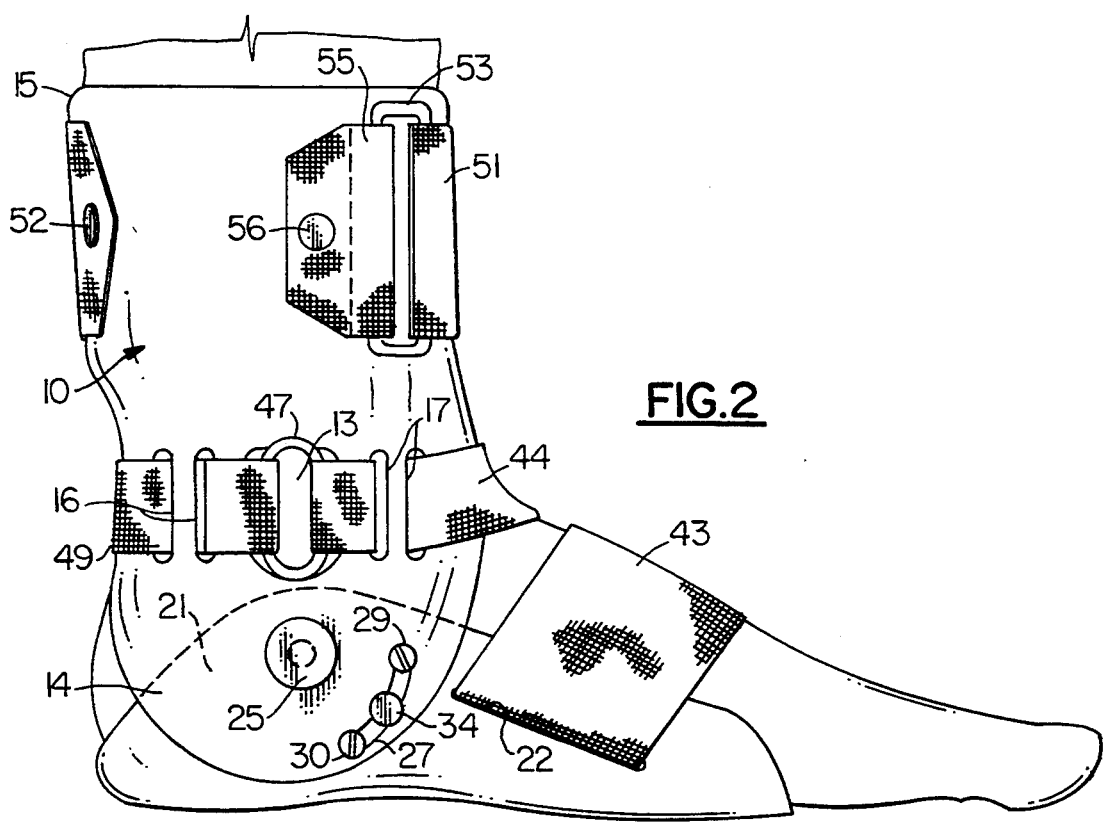
FIG. 2 is an elevation of the lateral side of the assembled therapeutic ankle orthosis of FIG. 1 showing the foot in horizontal position and with the locking means in place.

Formed in the lateral shell lower end portion 14 is a curved slot 27 centered about the axis of the rivet 23. As shown in FIG. 2 one end of the slot 27 is approximately horizontally forward of the pivot means provided by the rivet 23 and the other end of the slot 27 is at least about 45° downwardly and forwardly of that pivot means axis when the leg and foot are vertical and horizontal respectively. A first removable locking screw 29 extends through the upper end of the slot 27 into threaded engagement with the overlapping foot shell side portion 21. A second locking screw 30 extends through the lower end of the slot 27 also into threaded engagement with the overlapping foot shell side portion 21. When the locking screws 29 and 30 are in place as shown in FIG. 1 the user cannot pivot the foot shell 11 with respect to the lateral shell 10 either upwardly or downwardly to raise or lower the foot. At an appropriate stage in the therapy process when movement of the foot with respect to the leg is permissible, the lock screws 29 and 30 may be removed so that the foot can articulate as for example downwardly into the position shown in FIG. 3. If desired, the curved slot 27 may extend upwardly above a line horizontal with the axis of the rivet 23 when the leg is vertical and the foot is horizontal to permit the foot to be raised slightly above the horizontal while the leg is vertical.

Holding together the overlapping lower end portion 14 of the lateral shell 10 and the side portion 21 of the foot shell 11 is securing means comprising a post 33 extending slidably through the slot 27 intermediate the ends thereof when the leg and foot are vertical and horizontal respectively as shown in FIG. 2. A cap 34 is provided on the outer end of the post 33 for holding the lateral shell lower end portion 14 against the foot shell side portion 21 for reasons explained hereinafter.

Figure 5:
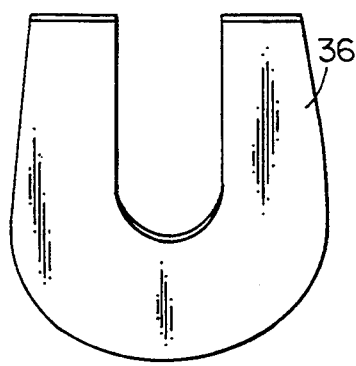
FIG. 5 is a side perspective view of the U-pad to be disposed on the inside of the lateral shell.
Figure 6:
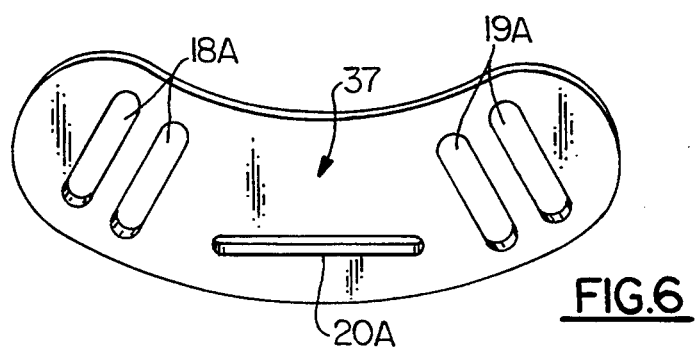
FIG. 6 is a side perspective view of the crescent pad to be disposed on the inside of the medial shell.

Shown in FIG. 5 is a U-pad 36 of self-supporting thermoplastic foam material. It is releasably secured to the inside of the lateral shell 10 by appropriate means such as quick-release hook-and-pile fastener patches sold under the trademark "Velcro". This U-shaped configuration provides an upwardly open channel for release of edema from around the fibular malleolus. A similar crescent-shaped pad 37 is provided as shown in FIG. 6 which conforms in all respects to the shape of the crescent-shaped medial shell 12, including the presence of paired slots 18A and 19A and a central slot 20A. It is the purpose of the crescent pad 37 to apply compression around the tibial malleolus and direct edema upwardly from that sensitive area.

Figure 7:
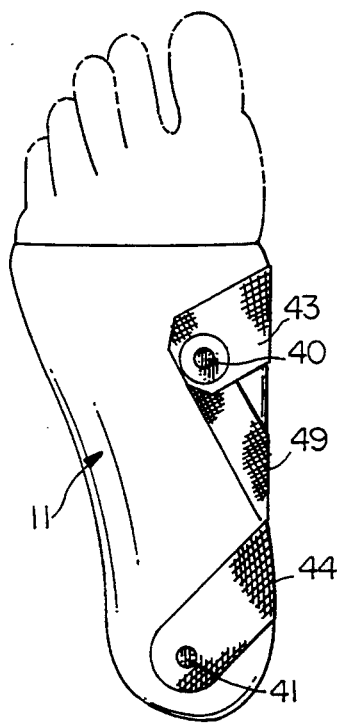
FIG. 7 is a plan view of the underside of the foot shell of the therapeutic ankle orthosis of the invention showing the connections of certain of the adjustable straps to the foot shell.

Referring to FIG. 7, rivets 40 and 41 are fixed to the medial underside of the forward and rearward portions respectively of the foot shell 11. The forward rivet 40 is shown securing the ends of two straps, though it may be appropriate to have each strap end secured by its own rivet. One is a foot strap 43 which can be crossed over the top of the mid foot and threaded through the slot 22 in the opposite lateral side of the forward portion of the foot shell 11. It can then be turned back upon and adjustably tightened and secured to itself by hook-and-pile fastener means such as that described previously.

The forward rivet 40 also secures one end of a first strap 44 which is threaded through the pair of slots 18 in the medial shell 12 and the corresponding slots 18A in the crescent pad 37 and then through the pair of slots 17 in the lateral shell 10. The strap 44 then is passed around a D-ring 47 which provides buckling means positioned above the overlapping shell portions 14 and 21. To be adjustably tightened the strap 44 may be turned back upon and attached to itself by hook-and-pile fastener means.

Secured by the rearward rivet 41 is a second strap 49 which is threaded through the pair of slots 19 in the medial shell 12 and the corresponding slots 19A in the crescent pad 37 and then around behind the ankle through the pair of slots 16 in the lateral shell 10. The remote end of the strap 49 is passed around the D-ring 47 and can be adjustably tightened by being turned back upon and secured to itself with the use of hook-and-pile fastener means.

Figure 3:
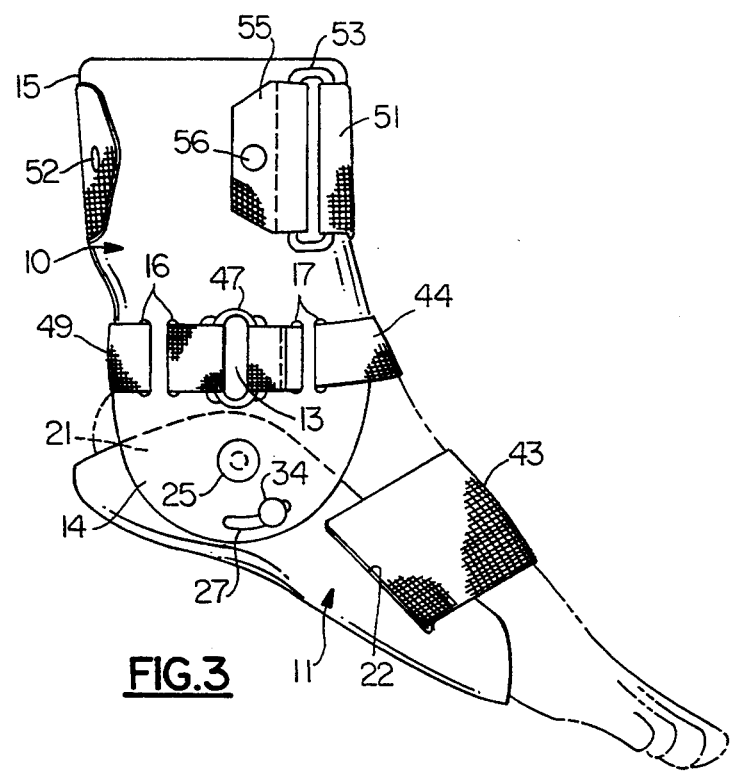
FIG. 3 is an elevation similar to FIG. 2 with the locking means removed and showing the foot turned downwardly.

In use as shown in FIGS. 2 and 3 the D-ring 47 overlies the aperture 14 in the lateral shell 10. By tightening the straps 44 and 49 compression can be applied to the lateral shell 10 and thus to the U-pad 36 to compress the ankle directly forwardly and rearwardly of the fibular malleolus which is where edema tends to accumulate as a consequence of an ankle sprain.

A leg strap 51 is affixed at one end by a rivet 52 to the upper posterior end of the lateral shell 10 and extends around and through a second D-ring 53. The strap 51 may be adjustably tightened by being turned back against and secured to itself by suitable hook-and-pile fastener means. The D-ring 53 is threaded through a hem in a short tab 55 of a material similar to the strap 51, the tab 55 being secured to the lateral shell 10 by a rivet 56. The rivets 52 and 56 not only anchor the strap 51 and tab 55 but permit angular movement around their respective points of attachment.

When the ankle orthosis of the invention is strapped to the foot as described above and as shown in FIGS. 1 to 3, several results are achieved. The U-pad 36 directs edema upwardly from around the fibular malleolus and compression is applied precisely where desired forwardly and rearwardly of the fibular malleolus. The medial shell 12 and the crescent pad 37 may be adjustable up and down and forwardly and rearwardly, with the first and second straps 44 and 49 sliding in their respective medial shell slots 18, 19 and 20 and crescent pad slots 18A, 19A and 20A to locate the medial shell properly relative to the user's tibial malleolus and direct edema upwardly from that area. Foot motion may be prevented by selected use of the locking screws 29 and 30 or permitted by their removal.

Figure 8:
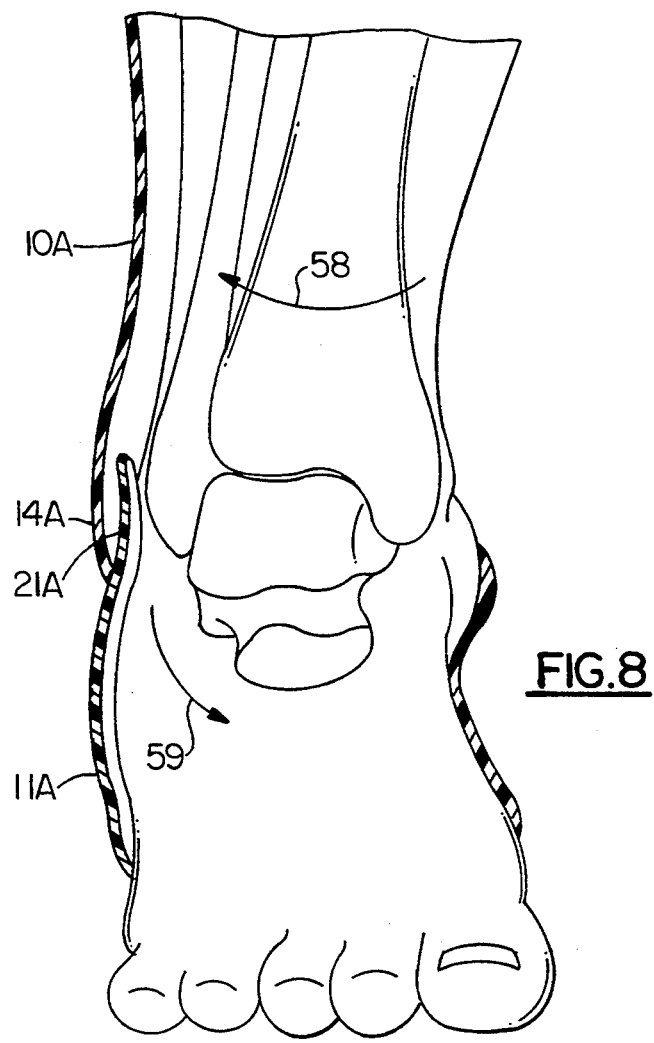
FIG. 8 is a somewhat schematic illustration of a foot viewed from the front showing those overlapping portions of the foot and lateral shells which tend to separate during rotation of the foot and leg in opposite directions in a horizontal plane, which separation is resisted by the structure of the invention.

Most importantly adduction or internal foot rotation combined with external leg rotation in a horizontal plane are prevented by the post 33 in the slot 27 and by the cap 34 on the end of the post 33. These serve as securing means which hold together the overlapping lower end portion 14 of the lateral shell 10 and the side portion 21 of the foot shell 11 forwardly of the pivot means provided by the rivet 23. The bio-mechanics of this are illustrated schematically in FIG. 8. If the foot and leg are rotated in opposite directions in a horizontal plane, the leg rotates in one direction as shown by the arrow 58 while the foot rotates in the opposite direction as shown by the arrow 59. A lower end portion 14A of a lateral shell 10A and the overlapping side portion 21A of a foot shell 11A will tend to move apart in the area forward of their point of pivoted connection. Since the cap 34 on the post 33 holds those overlapping shell portions 14 and 21 together in the area of the slot 27, effective protection is provided against adduction, involving internal foot rotation combined with external leg rotation. In the prior art German Petty Patent referred to earlier, the post is located directly beneath rather than forwardly of the fibular malleolus leaving the forward overlapping shell portions of that reference susceptible to spreading apart. Protection against adduction of the foot is substantially superior in this preferred embodiment of the invention to that of the prior art.

The scope of this invention is to be determined by the following claims rather than the foregoing description of a preferred embodiment.

I claim:
1. A therapeutic ankle orthosis comprising
   a) an extended lateral shell having an aperture adapted to receive the fibular malleolus and having a lower end portion extending downwardly beneath that aperture,
   b) a crescent-shaped medial shell adapted to fit beneath and upwardly about the tibial malleolus,
   c) a foot shell adapted to underlie the rear foot and having an upper lateral side portion extending upwardly to overlap the lower end portion of the lateral shell,
   d) pivot means connecting the lower end portion of the lateral shell to the side portion of the foot shell permitting angular movement of the foot shell relative to the lateral shell about an axis substantially coincident with the functional axis of the talocrual joint, e) locking means for selectively preventing angular movement of the foot shell relative to the lateral shell, f) securing means for holding together the overlapping lower end portion of the lateral shell and the side portion of the foot shell forwardly of the pivot means to resist ankle inversion and eversion, and g) adjustable strap means for holding the shells in operative position on the leg and ankle and foot.

2. A therapeutic ankle orthosis according to claim 1 wherein the lateral shell is contoured generally to fit the lower leg and ankle and includes a curved posterior leg brace portion.

3. A therapeutic ankle orthosis according to claim 1 wherein the lateral shell lower end portion overlaps the outside of the foot shell side portion.

4. A therapeutic ankle orthosis according to claim 3 wherein the pivot means is a rivet fixed to the foot shell side portion and extending outwardly through a hole in the overlapping lateral shell lower end portion and having a head holding the overlapping side and end shell portions together.

5. A therapeutic ankle orthosis according to claim 1 wherein a curved slot is formed in one of the overlapping lateral shell lower end portion and the foot shell side portion, the curve of the slot being centered about the axis of the pivot means, one end of the slot being approximately horizontally forward of the pivot means axis and the other end of the slot being at least about 45° downwardly and forwardly of the pivot means axis when the orthosis is positioned on a leg and foot and said leg and foot are positioned vertically and horizontally respectively.

6. A therapeutic ankle orthosis according to claim 5 wherein the slot is formed in the lateral shell lower end portion and the lower end portion overlaps the outside of the foot shell side portion.

7. A therapeutic ankle orthosis according to claim 5 wherein the locking means comprises removable locking screws extending through the slot at each end thereof into threaded engagement with the other of the overlapping lateral shell lower end portion and foot shell side portion.

8. A therapeutic ankle orthosis according to claim 7 wherein the slot is formed in the lateral shell lower end portion, said lower end portion overlapping the outside of the foot shell side portion, and the removable locking screws are in threaded engagement with the foot shell side portion.

9. A therapeutic ankle orthosis according to claim 5 wherein the securing means comprises a post affixed to the other of the overlapping lateral shell lower end portion and the foot shell side portion, the post extending through the slot intermediate the ends thereof when the leg and foot are vertical and horizontal respectively, and a cap on the outer end of the post for holding that shell portion in which the slot is formed against the other shell portion.

10. A therapeutic ankle orthosis according to claim 9 wherein the slot is formed in the lateral shell lower end portion, the lower end portion overlapping the outside of the foot shell side portion, and the post is affixed to the foot shell side portion.

11. A therapeutic ankle orthosis according to claim 1 wherein the strap means comprises a first strap fixed at one end to a forward portion of the foot shell and threaded through first slots in the medial shell and adjustably secured at its opposite end to buckling means above the overlapping shell portions, a second strap fixed at one end to a rearward portion of the foot shell and threaded through second slots in the medial shell and adjustably securable at its opposite end to said buckling means, a foot strap affixed at one end to one side of said foreward portion the foot shell and threaded through a slot in the opposite side of the foreward portion of the foot shell and turned back upon and adjustably secured to itself, and a leg strap affixed at one end to the upper portion of the lateral shell and adjustably secured at its opposite end to said upper portion of the lateral shell.

12. A therapeutic ankle orthosis according to claim 11 wherein the medial shell is movable up and down and forwardly and rearwardly with the first and second straps sliding in their respective medial shell first and second slots to locate the medial shell in a selected position relative to a user's tibial malleolus.

13. A therapeutic ankle orthosis according to claim 11 wherein the first and second and foot straps are affixed to the underside of the medial side of the forward portion of the foot shell.

14. A therapeutic ankle orthosis according to claim 11 wherein the buckling means securing the ends of the first and second straps overlies the lateral shell aperture.

15. A therapeutic ankle orthosis according to claim 1 which includes a U-pad disposed beneath and upwardly about the aperture of the lateral shell.

16. A therapeutic ankle orthosis according to claim 1 which includes a crescent pad on the inside of the medial shell.

17. A therapeutic ankle orthosis according to claim 1 wherein the shells are semi-rigid.

18. A therapeutic ankle orthosis comprising a) an extended lateral shell having an aperture adapted to receive the fibular malleolus and having a lower end portion extending downwardly beneath that aperture;

b) a foot shell adapted to underlie the rear foot and extend forwardly beyond the tarsal joints and having an upper lateral side portion extending upwardly to overlap the lower end portion of the lateral shell;

c) pivot means connecting the lower end portion of the lateral shell to the side portion of the foot shell permitting angular movement of the foot shell relative to the lateral shell about an axis substantially coincident with the functional axis of the talocrual joint; and d) locking means for selectively preventing angular movement of the foot shell relative to the lateral shell comprising i. a curved slot formed in one of the overlapping lateral shell lower end portion and foot shell side portion, the curve of the slot being centered about the axis of the pivot means, and one end of the slot being approximately horizontally forward of the pivot means axis and the other end of the slot being at least about 45° downwardly of the pivot means axis when the orthosis is positioned on the leg and foot and said leg and foot are positioned vertically and horizontally respectively, and ii. removable locking screws extending through the slot at each end thereof into threaded engagement with the other of the overlapping lateral shell lower end portion and foot shell side portion.

19. A therapeutic ankle orthosis according to claim wherein the slot is formed in the lateral shell lower end portion, said lower end portion overlapping the outside of the foot shell side portion, and the removable locking screws are in threaded engagement with the foot shell side portion.

20. A therapeutic ankle orthosis comprising
   a) an extended lateral shell having an aperture adapted to receive the fibular malleolus and having a lower end portion extending downwardly beneath that aperture;
   b) a foot shell adapted to underlie the rear foot and extend forwardly beyond the tarsal joints and having an upper lateral side portion extending upwardly to overlap the lower end portion of the lateral shell;
   c) pivot means connecting the lower end portion of the lateral shell to the upper side portion of the foot shell permitting angular movement of the foot shell relative to the lateral shell about an axis substantially coincident with the functional axis of the talocrual joint; and
   d) securing means for holding together the overlapping lateral shell lower end portion and the foot shell side portion forwardly of the pivot means to resist ankle inversion and eversion comprising
      i. a curved slot formed in one of the overlapping lateral shell lower end portion and foot shell side portion, the curve of the slot being centered about the axis of the pivot means, one end of the slot being approximately horizontally forward of the pivot means axis and the other end of the slot being at least about 45° downwardly and forwardly of the pivot means axis when the orthosis is positioned on the leg and foot and said leg and foot are positioned vertically and horizontally respectively,
      ii. a post affixed to the other of the overlapping lateral shell lower end portion and the foot shell side portion, the post extending through the slot intermediate the ends thereof when the leg and foot are vertical and horizontal respectively, and
      iii. a cap on the outer end of the post for holding that shell portion in which the slot is formed against the other shell portion.

21. A therapeutic ankle orthosis according to claim 20 wherein the slot is formed in the lateral shell lower end portion, the lower end portion overlaps the outside of the foot shell side portion, and the post is affixed to the foot shell side portion.

22. A therapeutic ankle orthosis comprising
   a) an extended lateral shell having an aperture adapted to receive the fibular malleolus and having a lower end portion extending downwardly beneath that aperture,
   b) a rigid crescent-shaped medial shell adapted to fit beneath and upwardly about the tibial malleolus,
   c) a foot shell adapted to underlie the rear foot and extend forwardly beyond the tarsal joints and having an upper lateral side portion extending upwardly to overlap the lower end portion of the lateral shell,
   d) adjustable strap means for holding the shells in operative position on the leg and ankle and foot comprising
      i. a first strap fixed at one end to a forward portion of the foot shell and threaded through first slots in the medial shell and adjustably secured at its opposite end to buckling means above the overlapping shell portions, a second strap fixed at one end to a rearward portion of the foot shell and threaded through second slots in the medial shell and adjustably securable at its opposite end to said buckling means, a foot strap affixed at one end to one side of said forward portion of the foot shell and threaded through a slot in the opposite side of the foreward portion of the foot shell and turned back upon and adjustably secured to itself, and a leg strap affixed at one end to the upper portion of the lateral shell and adjustably secured at its opposite end to-said upper portion of the lateral shell.

23. A therapeutic ankle orthosis according to claim 22 wherein the medial shell is movable up and down and forwardly and rearwardly with the first and second straps sliding in their respective medial shell first and second slots to locate the medial shell in a selected position relative to a user's tibial malleolus.

24. A therapeutic ankle orthosis according to claim 22 wherein the first and second and foot straps are affixed to the underside of the medial side of the forward portion of the foot shell.

25. A therapeutic ankle orthosis according to claim 22 wherein the buckling means securing the ends of the first and second straps overlies the lateral shell aperture.

26. A therapeutic ankle orthosis comprising
   a) a rigid lateral shell having an aperture adapted to receive the fibular malleolus and having a lower end portion extending downwardly beneath that aperture, the lateral shell being contoured generally to fit the lower leg and ankle and including a curved posterior leg brace portion;
   b) a U-pad disposed beneath and upwardly about the aperture of the lateral shell and releasably secured to the inside of the lateral shell;
   c) a rigid crescent-shaped medial shell adapted to fit beneath and upwardly about the tibial malleolus;
   d) a crescent pad covering and being releasably secured to the inside of the medial shell;
   e) a foot shell adapted to underlie the rear foot and extend forwardly beyond the tarsal joint and having an upper lateral side portion extending upwardly to overlap behind the lower end portion of the lateral shell;
   f) pivot means connecting the lower end portion of the lateral shell to the upper side portion of the foot shell permitting angular movement of the foot shell relative to the lateral shell about an axis substantially coincident with the functional axis of the talocrual joint, the pivot means comprising a rivet fixed to the foot shell side portion and extending outwardly through a hole in the overlapping lateral shell lower end portion and having a head holding the overlapping side and end shell portions together;
   g) a curved slot formed in the overlapping lateral shell lower end portion, the curve of the slot being centered about the axis of the pivot means, one end of the slot being approximately horizontally forward of the pivot means axis and the other end of the slot being at least about 45° downwardly and forwardly of the pivot means axis when the orthosis is positioned on the leg and foot and said leg and foot are positioned vertically and horizontally respectively, h) locking means for selectively preventing angular movement of the foot shell relative to the lateral shell comprising removable locking screws extending through the slot at each end thereof into threaded engagement with the overlapping foot shell side portion;

i) securing means for holding together the overlapping lower end portion of the lateral shell and the side portion of the foot shell forwardly of the pivot means to resist ankle inversion and eversion comprising a post affixed to the foot shell side portion and extending through the slot intermediate the ends thereof when the orthosis is positioned on the leg and foot and said leg and foot are positioned vertically and horizontally respectively, and a cap on the outer end of the post for holding the lateral shell lower end portion against the foot shell side portion; and j) adjustable strap means for holding the shells in operative position on the leg and ankle and foot.

27. A therapeutic ankle orthosis according to claim 26 wherein the strap means comprises a first strap fixed at one end to a forward portion of the foot shell and threaded through first slots in the medial shell and adjustably secured at its opposite end to buckling means above the overlapping shell portions, a second strap fixed at one end to a rearward portion of the foot shell and threaded through second slots in the medial shell and adjustably securable at its opposite end to said buckling means, a foot strap affixed at one end to one side of said forward portion of the foot shell and threaded through a slot in the opposite side of the foreward portion of the foot shell and turned back upon and adjustably secured to itself, and a leg strap affixed at one end to the upper portion of the lateral shell and adjustably secured at its opposite end to said upper portion of the lateral shell.

28. A therapeutic ankle orthosis comprising
a) a semi-rigid side shell adapted to fit in operative position against the ankle of a user,
b) said side shell having an aperture adapted to receive a malleolus of the user,
c) a U-pad releasably secured to the inside of said shell to be disposed beneath and upwardly about the aperture of the shell,
d) a foot shell adapted to underlie the rear foot of the user and having an upper side portion extending upwardly to overlap and connect to a lower end portion of the side shell, and
e) adjustable strap means for holding the side shell and pad in said operative position comprising a first strap fixed at one end to a forward portion of the foot shell and threaded through first slots in the side shell and adjustably secured at its opposite end to securing means above the overlapping shell portions, and a second strap fixed at one end to a rearward portion of the foot shell and threaded through second slots in the side shell and adjustably secured at its opposite end to said securing means.

29. A therapeutic ankle orthosis comprising
a) an extended side shell having an aperture adapted to receive a malleolus and having a lower end portion extending downwardly beneath that aperture,
b) a foot shell adapted to underlie the rear foot and having an upper side portion extending upwardly to overlap the lower end portion of the side shell,
c) pivot means connecting the lower end portion of the side shell to the side portion of the foot shell permitting angular movement of the foot shell relative to the side shell about an axis substantially coincident with the functional axis of the talocrual joint,
d) locking means for selectively preventing angular movement of the foot shell relative to the side shell,
e) securing means for holding together the overlapping lower end portion of the side shell and the side portion of the foot shell forwardly of the pivot means to resist ankle inversion and eversion, and
f) adjustable strap means for holding the shells in operative position on the ankle and foot comprising a first strap fixed at one end to a forward portion of the foot shell and threaded through first slots in the side shell and adjustably secured at its opposite end to securing means above the overlapping shell portions, and a second strap fixed at one end to a rearward portion of the foot shell and threaded through second slots in the side shell and adjustably secured at its opposite end to said securing means.

* * * * *